United States Patent
Rowley Grant et al.

(10) Patent No.: US 10,950,343 B2
(45) Date of Patent: Mar. 16, 2021

(54) HIGHLIGHTING BEST-MATCHING CHOICES OF ACQUISITION AND RECONSTRUCTION PARAMETERS

(71) Applicant: Siemens Healthcare GmbH, Erlangen (DE)

(72) Inventors: Katharine Lynn Rowley Grant, Rochester, MN (US); Bernhard Schmidt, Furth (DE)

(73) Assignee: Siemens Healthcare GmbH, Erlangen (DE)

( * ) Notice: Subject to any disclaimer, the term of this patent is extended or adjusted under 35 U.S.C. 154(b) by 171 days.

(21) Appl. No.: 15/637,152

(22) Filed: Jun. 29, 2017

(65) Prior Publication Data
US 2019/0005199 A1 Jan. 3, 2019

(51) Int. Cl.
| | |
|---|---|
| *G06F 17/00* | (2019.01) |
| *G16H 40/63* | (2018.01) |
| *G16H 50/70* | (2018.01) |
| *G16H 30/20* | (2018.01) |
| *G06F 3/0484* | (2013.01) |
| *G06F 3/0482* | (2013.01) |
| *G06F 3/0488* | (2013.01) |

(52) U.S. Cl.
CPC ......... *G16H 40/63* (2018.01); *G06F 3/04847* (2013.01); *G16H 30/20* (2018.01); *G16H 50/70* (2018.01); *G06F 3/0482* (2013.01); *G06F 3/0488* (2013.01)

(58) Field of Classification Search
CPC ........ G16H 40/63; G16H 30/20; G16H 50/70; G06F 3/0482; G06F 3/0488; G06F 3/04847; G06F 3/0485; A61B 6/545; A61B 6/5294; A61B 8/5292

See application file for complete search history.

(56) References Cited

U.S. PATENT DOCUMENTS

| | | | |
|---|---|---|---|
| 6,287,257 B1* | 9/2001 | Matichuk | A61B 8/00 600/437 |
| 7,254,623 B1* | 8/2007 | Toth | A61B 6/032 707/999.005 |
| 8,000,510 B2* | 8/2011 | Boeing | A61B 6/482 382/128 |
| 2003/0095150 A1* | 5/2003 | Trevino | G01R 33/546 715/810 |
| 2007/0168877 A1* | 7/2007 | Jain | G06F 3/0482 715/772 |
| 2009/0226060 A1 | 9/2009 | Gering et al. | |
| 2009/0279672 A1* | 11/2009 | Reiner | A61B 6/581 378/207 |
| 2010/0040268 A1* | 2/2010 | Boeing | A61B 6/482 382/128 |
| 2010/0145182 A1* | 6/2010 | Schmidt | G06Q 50/22 600/410 |

(Continued)

*Primary Examiner* — Cesar B Paula
*Assistant Examiner* — James H. Blackwell (57) ABSTRACT

Systems and methods are provided for indicating recommended settings for data acquisition in a medical scanner. A scan protocol including a first parameter is identified. A first subset of values is determined for the first parameter as a function of the scan protocol. A first plurality of values is displayed for the first parameter with the first subset of values highlighted. A first selection is received of a first selected value for the first parameter. Image data is generated using the first selection.

13 Claims, 7 Drawing Sheets

(56) References Cited

U.S. PATENT DOCUMENTS

| | | | | |
|---|---|---|---|---|
| 2011/0022981 | A1* | 1/2011 | Mahajan | A61N 1/37247 715/810 |
| 2011/0110572 | A1* | 5/2011 | Guehring | A61B 6/5258 382/131 |
| 2011/0153255 | A1* | 6/2011 | Horger | A61B 5/055 702/104 |
| 2012/0213326 | A1* | 8/2012 | Walker | A61B 6/032 378/4 |
| 2012/0213336 | A1* | 8/2012 | Liddiard | G21K 1/02 378/161 |
| 2013/0311472 | A1* | 11/2013 | Cohen-Solal | G06F 19/321 707/737 |
| 2014/0098932 | A1* | 4/2014 | Profio | A61B 6/032 378/19 |
| 2014/0177788 | A1 | 6/2014 | Stevens et al. | |
| 2014/0177803 | A1* | 6/2014 | Stevens | A61B 6/52 378/98 |
| 2014/0348401 | A1* | 11/2014 | Xu | A61B 6/545 382/128 |
| 2015/0100572 | A1* | 4/2015 | Kalafut | G06Q 50/24 707/736 |
| 2015/0142457 | A1* | 5/2015 | Marshall | G16H 50/50 705/2 |
| 2015/0199478 | A1* | 7/2015 | Bhatia | A61B 6/488 382/128 |
| 2015/0216440 | A1* | 8/2015 | Senegas | G16H 40/63 600/408 |
| 2016/0231396 | A1* | 8/2016 | Sunaga | A61B 5/055 |
| 2016/0328246 | A1* | 11/2016 | Broz | G06N 5/02 |
| 2016/0328631 | A1 | 11/2016 | Lay et al. | |

\* cited by examiner

HIGHLIGHTING BEST-MATCHING CHOICES OF ACQUISITION AND RECONSTRUCTION PARAMETERS

BACKGROUND

The present embodiments relate to providing guidance for performing medical imaging tasks. Different medical imaging systems use different settings and parameters for acquisition and reconstruction of images. For a computed tomography (CT) example, to reach a task and user-specific image quality, a user has to select optimized parameters for CT acquisition and corresponding reconstruction choices. Currently, there is limited guidance as to which parameter settings are good or reasonable.

A similar situation occurs when protocols and reconstruction settings are transferred from one scanner to another scanner. In a medical environment, as various imaging systems are different (for example, different manufacturer, models, software versions), an exact match of parameter settings is often not possible. Users may have to discover optimal parameter settings on their own from lists of parameters. The discovery process may not be reasonable from a safety perspective or for producing a subjectively good, desirable image quality. Instead of providing just lists of options for the different parameters, some guidance is needed for improved image quality, consistency, and workflow optimization.

SUMMARY

By way of introduction, the preferred embodiments described below include methods, systems, instructions, and non-transitory computer readable media for providing visual guidance for selecting parameters on a medical scanner. Recommendations for scan parameters (acquisition and/or reconstruction) are provided to a user. As a perfect match may not be possible, a range of inter-connected choices are provided. The inter-connections and range of choices are defined using prior scans, matching techniques, and deep machine-learning.

In a first aspect, a method is provided for indicating recommended settings for data acquisition in a medical scanner. A scan protocol including a first parameter is identified. A first subset of values is determined for the first parameter as a function of the scan protocol. A first plurality of values is displayed for the first parameter with the first subset of values highlighted. A first selection is received of a first selected value for the first parameter. Image data is generated using the first selection.

In a second aspect, a method is provided for providing guidance for generating a scan image. A first value of a first scan parameter is identified for a first medical scanner. A set of second values is determined for a second scan parameter for a second medical scanner. The set of second values is displayed as highlighted choices. A selection of a second value is received from the set of second values. The scan image is generated using the selection.

In a third aspect, a system is provided for guidance for selecting a value for a parameter in a medical scanner. The system includes a memory, a processor, and a display. The memory is configured to store a plurality of previous scans and first values for a parameter for each of the previous scans. The processor is configured to identify one or more recommended values of the first values for the parameter based on the plurality of previous scans. The display is configured to display the one or more recommended values differently than other values for selection by a user.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Embodiments provide visually recommended settings for data acquisition and/or reconstruction. In current imaging systems, preset scan protocols may be provided that include values for performing a scan. Recommendations for optimal parameter settings may be provided to a user during initial training by an applications specialist. Based on the specialist's experience and recommendations, settings are selected by a user. In addition, users may try different combinations of settings, with the hope of finding an optimal parameter set for their particular image quality specifications. However, typically, no guidance is provided.

Parameters for performing an image scan and reconstruction of an image from the scan may be extensive and complex. Preset scan protocols providing default values for the parameters may provide standard options for performing a scan. However, preset scan protocols do not allow for adjustments or experimentation with the parameters. Additionally, certain users prefer different images outcomes. With a preset protocol, the user may not be able to find an image view that the user prefers, instead the user may only be able to select protocols that were set previously. As such, preset protocols limit the ability to provide a quality scan. Different protocols may further be better for different patients or specific scans. For example, for a full body scan, parameters may need to be adjusted to provide good images for varying body sizes. A preset protocol provides a one size fits all scheme. In scenarios where a preset protocol allows for some adjustment, there is little to no guidance of the relationships between adjusting one parameter and how the adjustment affects other parameters.

In an embodiment, guidance is provided for selecting scan acquisition and/or reconstruction parameters. Visually distinctive choices may be provided for a user with a clear indication of which choice or choices will result in high quality images. The guidance may further be used in a case of scan protocol transfer between systems of different types or different vendors. For a user who operates multiple scanner models, e.g. from multiple manufacturers, the variability in names for scan acquisition and reconstruction parameters may lead to confusion, reduced comfort, and an increased potential for error. Often an exact match is not possible. The scale of values or the terminology is distinct for each manufacturer or model, thus any selection proposed by the machine might not be "correct" relative to another machine. Providing a range of parameters with a clear guidance may be beneficial to the user for making a decision.

In an example, the system recommends values for parameters that are compatible and recommended based on previous scans instead of merely providing a long arbitrary list of choices. Previous choices and resulting image quality may be tracked. Machine learning may be used to determine recommended (or reasonable) settings in a population of similar acquisitions, or similar image quality requirements for certain applications. For example, in case of thick slices, sharp image reconstruction parameters might not be recommended, and thus automatically softer reconstruction parameters may be recommended. If, however, a thin slice reconstruction is desired, different choices may be highlighted. The recommendation and highlighting of parameters may be applied to scanning, reconstruction, or both scanning and reconstruction parameters.

Figure 1:
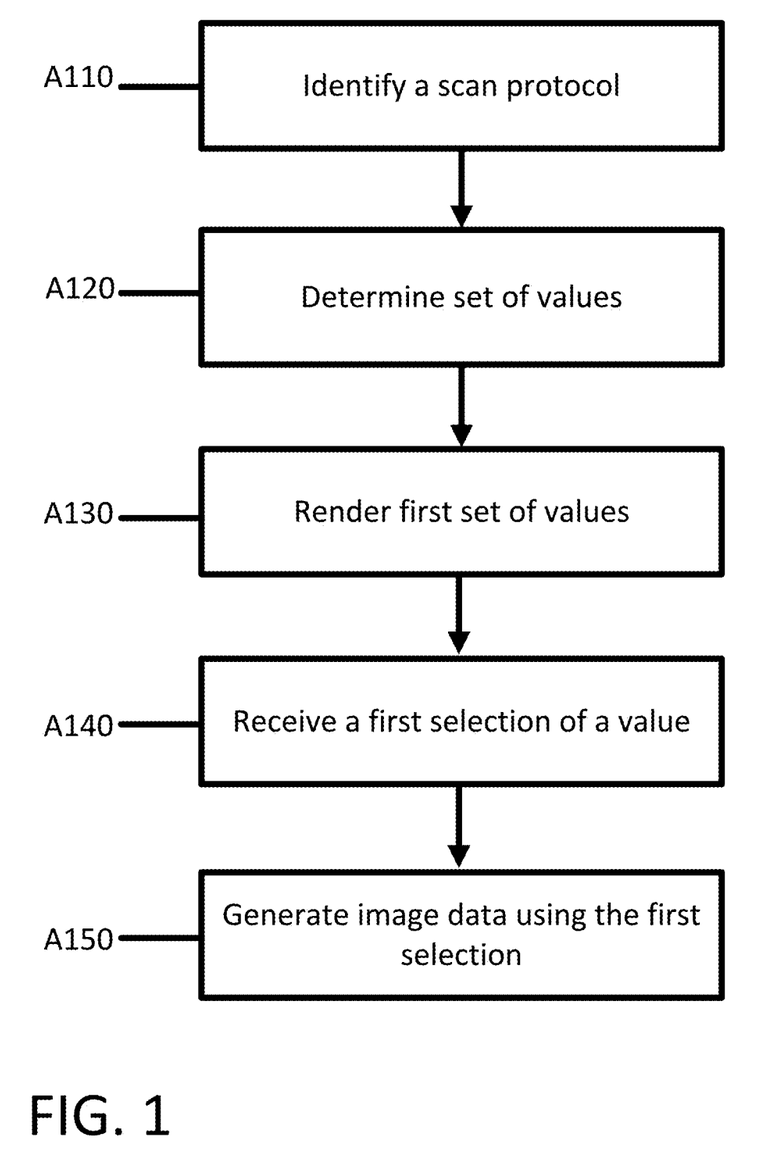
FIG. 1 illustrates one embodiment of a method for providing visual guidance for selecting scan parameters.

FIG. 1 illustrates one embodiment of a method for providing guidance for imaging scans. The process includes the analysis of stored data sets from previous scans to determine recommended values for one or more parameters. The recommend values are provided to a user in a visually distinctive manner. The user selects a value and one or more images are generated. The generated image(s) are medical imaging data.

Figure 7:
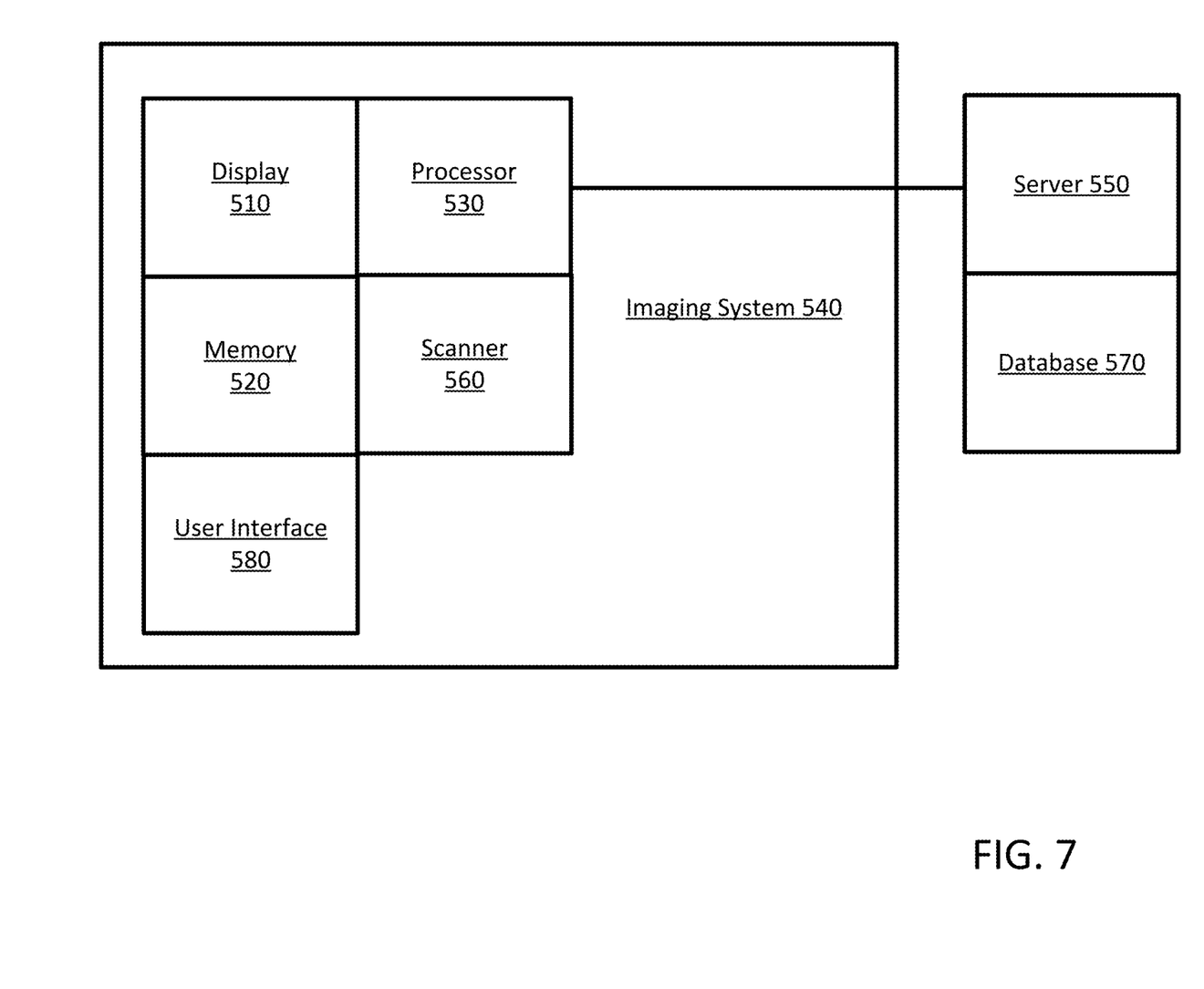
FIG. 7 is a block diagram of one embodiment of a system for providing visual guidance for selecting scan parameters.

The acts are performed by the system of FIG. 7, other systems, a medical scanner, a workstation, a computer, and/or a server. For example, A150 is performed by a medical scanner. Act A120 is performed by a processing component, such as the medical scanner, a workstation, or a computer. The acts are performed in the order shown (e.g., top to bottom) or other orders.

In act A110, a scan protocol is identified. The scan protocol is based on the type of scan. The type of scan may be based on the type of object or method of scanning to be performed. A user may enter the type of scan into the imaging system or select an option on a screen of the image system. For example, the user selects an application.

The type of scan may include one or more different scan protocols. The scan protocols may include values for multiple acquisition parameters for acquiring image data. After the acquisition of scan data, image reconstruction parameters may be used to generate an image for display or use by the user.

Any type of medical image and corresponding medical scanner may be used to generate the images. In one embodiment, the medical image is a computed tomography (CT) image acquired with a CT system. For CT, the raw data acquired with the detector using acquisition parameters is reconstructed into a three-dimensional representation using reconstruction parameters. In another embodiment, magnetic resonance (MR) data representing a patient is acquired. MR data is acquired with an MR system. The data is acquired using a pulse sequence for using settings defined by values of acquisition parameters. For MR, the magnetic resonance data is k-space data. Fourier analysis is performed to reconstruct the data from the k-space into a three-dimensional object or image space. In yet another embodiment, the generated scan image data may be ultrasound data. Beamformers and a transducer array scan a patient acoustically using setting with values of acquisition parameters. The acquired polar coordinate data is detected and processed into ultrasound data representing the patient based on values for acquisition parameters. In other embodiments, the acquired data may be positron emission tomography (PET), single photon emission computed tomography (SPECT), or other nuclear imaging data. Radioactive emissions from within the patient are detected using settings with values of acquisition parameters and reconstructed using settings with values of reconstruction parameters.

The generated medical image represents tissue and/or bone structure of the patient. Alternatively, the medical image represents flow, velocity, or fluids within the patient. In other embodiments, the medical image represents both flow and structure. For PET and SPECT, the scan data represents function of the tissue, such as uptake.

A scan protocol may provide some guidance to a user in that certain types of scans use specific ranges of parameters due to the region scanned or the purpose of the scan. In an example, a body scan may have different ranges of values for scanning parameters and reconstruction parameters than a head scan. The type of scan may limit the possible choices to a range of values that are physically viable and safe for a patient. For certain scan types and scan protocols, the scan protocols may include one or more predetermined values for one or more parameters. The reconstruction parameters may then be set to determine the outcome of the image. For example, certain scans may be provided to a user with predefined values for a number of parameters. The inability to adjust the scan protocol may be a safety measure in order to prohibit damaging the object being scanned. The user may thus select one or more scan protocols from a menu. Once the scan protocol is selected, the user may have the option to select different reconstruction protocols that are based on the scan protocol selection.

For different types of scan protocols, certain parameters may be aggregated into single selections. For example, instead of ten different parameters for a user to select, the system may present only four parameters. The four parameters may be generated using a minimization model from values of the ten parameters. The four parameters that are displayed may provide different values that represent combinations of the previous grouping of parameters.

For a CT scan, example types of scan acquisition parameters may include tube current, tube current-time product, energy (kV), exposure (mAs) trot, pitch, and data (mm) among others. A tube current value, for example, defines number of electrons accelerated across an x-ray tube per unit time, expressed in units of milliampere (mA). Increases in tube current or the product of tube current and scan time (mAs) result in improved image quality, decreased image noise, and increased patient dose. The tube current-time product represents the product of tube current and exposure time per rotation, expressed in units of milliampere times seconds (mAs). In axial scan mode, the tube current-time product is equal to tube current×(scan angle÷360)×rotation time. In helical scan mode, the tube current-time product is equal to tube current×rotation time. The parameter pitch may be used to describe the table travel during helical CT;

equal to table travel (mm) per gantry rotation÷total nominal beam width (mm). Different scanning systems may use different terms or units for different scan acquisition parameters. Different scanning systems may use more or less scan acquisition parameters.

For reconstruction parameters in CT, the user may select values that define the processing of the scan data into an image. Image reconstruction impacts image quality and therefore radiation dose. For a given radiation dose, it is desirable to reconstruct images with the lowest possible noise without sacrificing image accuracy and spatial resolution. Reconstructions that improve image quality can be translated into a reduction of radiation dose because images of the same quality can be reconstructed at lower dose. Selection of reconstruction parameters may depend on the scan type or scan acquisition parameters. In certain embodiments, a kernel (also referred to as an algorithm or filter) may be used to bundle together multiple parameters into a preset group. Different kernels may provide different levels of image quality. For each kernel, there is a tradeoff between spatial resolution and noise. A smoother kernel generates images with lower noise but with reduced spatial resolution. A sharper kernel generates images with higher spatial resolution, but increases the image noise.

With a kernel, a user may only need to select one option when deciding upon reconstruction parameters. For example, when using a Siemens CT scanner, a user may not need to select individual values for parameters, but may select a single kernel. Each kernel may represent a set group of values for parameters for a specific type of scan. While the number of selections is reduced by using kernels, a user may not be given any guidance on which kernel to select. Due to the vast number of possibilities, multiple kernels may be reasonable or useful for a scan. In addition, even with the use of kernels, a user may adjust granular parameters inside the kernel to allow for experimentation and minor adjustment.

Another reconstruction parameter for CT is slice thickness. Slice thickness controls the spatial resolution in the longitudinal direction, influencing the tradeoffs among resolution, noise, and radiation dose. Users attempt to select the most appropriate reconstruction kernel and slice thickness for each clinical application so that the radiation dose may be minimized consistent with the image quality needed for the examination. Additional reconstruction parameters may be used in a scan. Different scanners may provide fewer or more options.

At act A120, a first subset of values for the first parameter are determined as a function of the type of scan protocol. The subset of values may be identified by analyzing prior scans or recommended settings for similar scan protocols. Prior scans and parameters used for the prior scans may be recorded and stored. In certain embodiments, the prior scans may be annotated with a quality score or attribute. For example, a prior scan using a first set of values for a set of parameters may result in an image with a sharpness level of 5 out of 6. Analysis of the prior scan along with other prior scans may identify which values in the set of values is likely to result in similar scans, e.g. scan with sharpness levels of 5 or 6 out of 6. Alternatively, the system may identify the last scans (e.g. the final selection) as acceptable scans based on a quality level for a specific use. For example, a prior scan using a set of values for a set of parameters may be identified as acceptable for scanning a neck of a patient. The prior scans, prior parameters, and results may be analyzed to determine the values of parameters that result in recommended or useful scan images. Different types of analysis may be used depending on the level and complexity of the prior scan data.

Statistical analysis or decision trees may be used to identify statistical similarity in the prior scan data by employing linear mathematical models or simple conditional logic. Data mining techniques may be used to identify in the prior scan data, the probabilistic occurrence of a sequence of events with other events. Data mining techniques may be trained in an unsupervised manner.

Advanced modeling systems may be used to analyze the prior scan data, such as regression analysis or deep learning though neural networks. Regression analysis is a statistical process for estimating the relationships among variables. Regression analysis may be used to identify the strength of the relationship between two variables in the prior scan data such as how the quality of an image is related to input power. Regression takes a group of random variables in the prior scan data, thought to be predicting an outcome, and tries to find a mathematical relationship between the variables.

Machine learning and deep learning may use neural networks to analyze the prior scan data. Neural networks may be made up of a collection of interconnected processing nodes. The connections between the nodes may be dynamically weighted. Neural networks employ a technique of learning relationships through repeated exposure to data and adjustment of internal weights. Neural networks allow quick model development and automated data analysis. Neural networks provide statistical modeling that is capable of building models from data containing both linear and non-linear relationships. While similar in concept to regression analysis, neural networks may capture nonlinearity and interactions among independent variables without pre-specification. Whereas traditional regression analysis requires that nonlinearities and interactions be detected and specified manually, neural networks perform the tasks automatically.

A generative model is a deep learnt model using restricted Boltzmann machines, deep belief network, neural autoregressive density estimators, auto-encoders, extensions thereof, or other deep learning approaches for modeling. In one embodiment, the trained deep generative model is a deep neural network with a set of j convolutional layers and k fully connected layers, each followed by a non-linear activation function, and a set of pooling layers for features reduction. Other layer arrangements may be used to analysis the prior scan data.

The analysis of the prior scan data may result in additional information other than the set of values for a parameter. Each value within the set of values may have a specific score associated with the value. For example, within a set of three values, the first value may be a most recommended value, and the second value may be the least recommended of the three.

The analysis of the prior scan data may further provide interrelationships between different parameters and interrelationships between values of the different parameters. For example, the analysis may identify that a first selection of a value for a first parameter alters the selection of a second value of a second parameter.

At act A130, the first parameters are displayed with the first subset of values highlighted. Different visual indicators may be used to indicate different advantages or information relating to the different values. Highlighting or shading may provide a visual indication of a level of quality or reasonableness. Different visual techniques may be used to indicate the type of outcome that results from a selection. For example, expected levels of quality or size of the image may be displayed or indicated with the different selections of values.

Figure 2A:
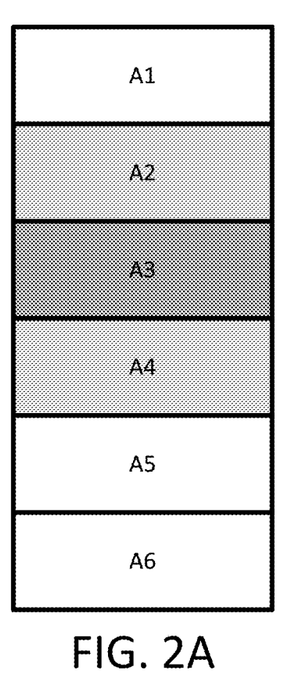
FIGS. 2A-2D illustrate examples of visual guidance for selecting scan parameters.

FIGS. 2A-2D depicts an example of the first subset of values highlighted. As depicted, the values range from A1-A6. The values may be rendered and displayed in numerical order, e.g. A1<A2<A3 etc. For FIGS. 2A-2D, the recommended values are shaded differently. For example, A3 in FIG. 2A is the most recommended value and as such is shaded the darkest. In FIG. 2A, the values A2 and A4 are also shaded (although less so than A3). The values A2 and A4 are also recommended, though less so than A3. The shading clearly indicates to a user that all three values A2-A4 would be recommended. A user does not need to understand the nature of the parameters to select a recommended value.

Figure 2B:
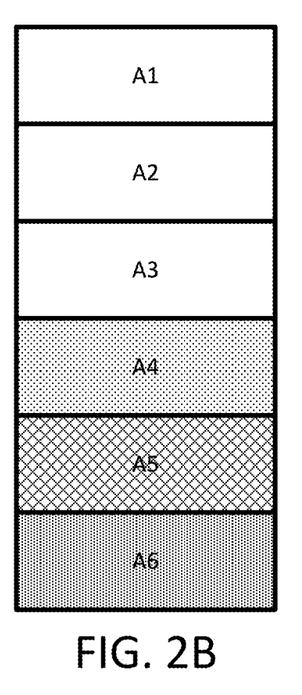

FIG. 2B depicts a second type of visual indicator. A5 is the most recommended value and indicated as such by a cross hatching. Different colors or visual indications may imply different outcomes. Different levels of intensity may imply different outcomes or levels of recommendations. For example, in FIG. 2B as opposed to FIG. 2A, a level of shading or highlighting may indicate a different outcome. One selection may be better for sharpness and another value for contrast. The visual indicator may indicate a level of recommendation or quality. For example, the intensity of the shading or color may indicate a more recommended value.

Figure 2C:
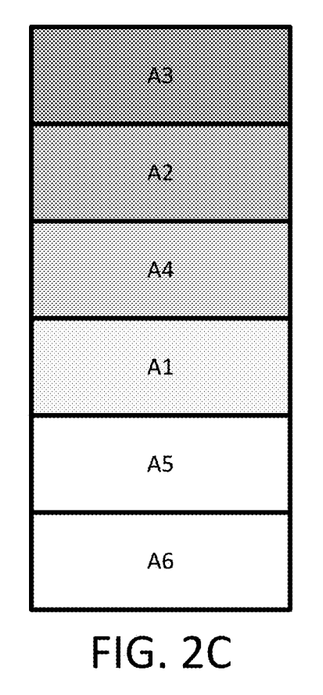
Figure 2D:
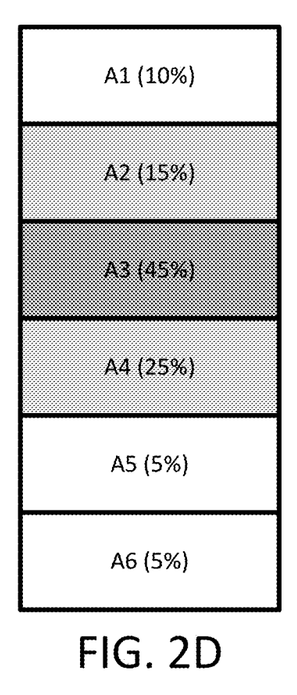

FIG. 2C depicts the values of FIG. 2A but rendered and displayed in a different order. In FIG. 2C, the values are ordered not numerically, but in descending order of quality (for example, if the shading is based off a level of quality). In FIG. 2C, based on feedback derived from previous scans, A3 is the most recommended value followed by A2, A4, A1, A5, then A6. FIG. 2D depicts the same recommendations of FIGS. 2A and 2C with additional information included. In FIG. 2D, a percentage is listed next to the values to allow a user to make a more educated selection. Based on previous scans, the value A3 was selected 45% of the time; the value A2, 15% of the time and so on.

At act A140, a value of the first set of values is selected. A user may select the value using an input device such as a touchscreen, keyboard, or microphone. When selected, the value may be displayed with an additional visual indicator such as a different highlight or border.

In an embodiment, more than one selection of parameters is made by a user. Ranges of values of subsequent parameters may be identified by machine learning or statistical techniques using as input prior scans and the first selection. The user selection of the value for one parameter may be used to determine the options and relative weighting of values for another parameter. The subsequent parameters may be scan acquisition parameters or scan reconstruction parameters. In an embodiment, the first selection relates to scan acquisition parameters and a second selection is made by the user for reconstruction parameters.

Figure 3:
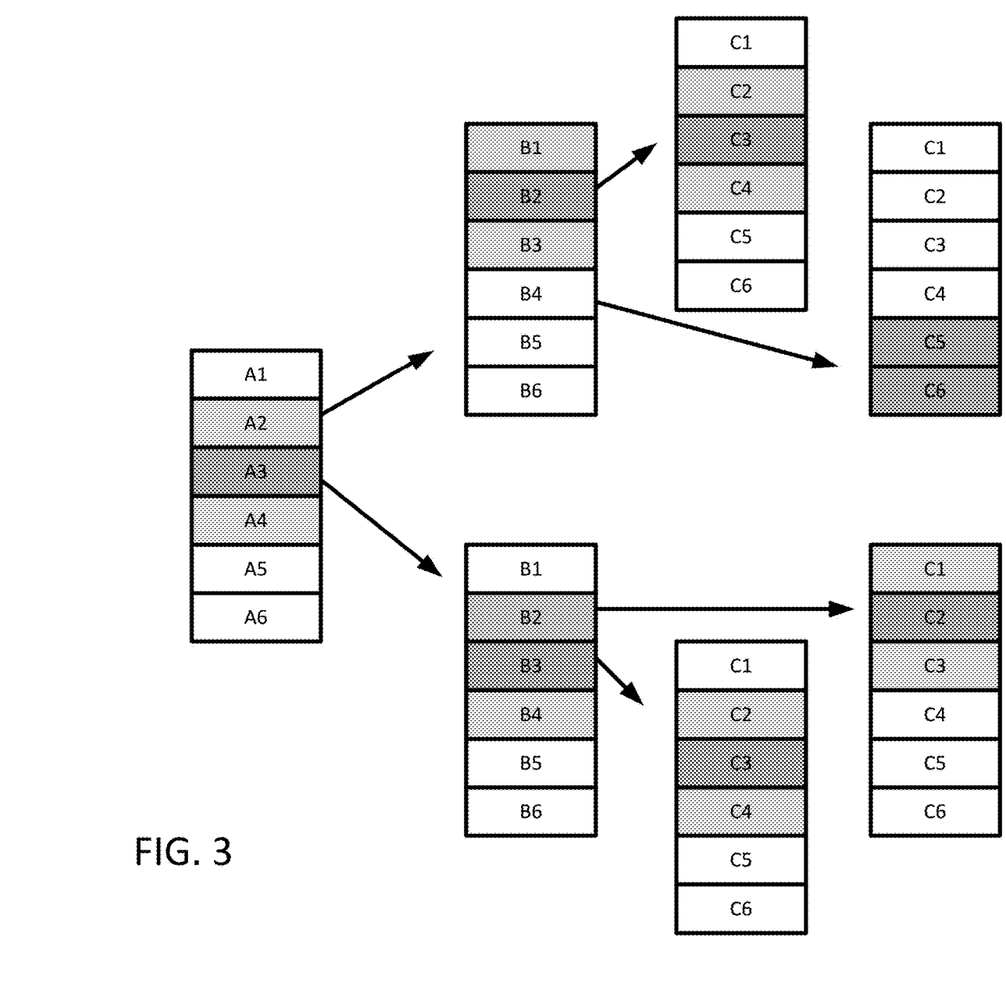
FIG. 3 illustrates a flow chart of one embodiment of providing visual guidance for selecting scan parameters.

FIG. 3 depicts presentation of options for three parameters for performing an image scan. The parameters A, B, and C may be scan acquisition parameters or reconstruction parameters. Similar to determining a first set values in act A120, the second values and third values may be identified through the use of machine learning or other statistical techniques. Different first selections for A may result in different recommended ranges for B and C. For example, as depicted in FIG. 3, a selection of A2 results in a recommended range of values B1, B2, and B3. A selection of B2 results in a recommended range of values C2, C3, and C4. Alternatively, a selection of value B4 results in a recommended range of values C5 and C6. If, however, A3 is selected, the recommended values for B are B2-B4. If B2 is then selected, the recommended values for C are C1-C3. If B3 is selected, then the recommended values for C are C2-C4. Each selection of a parameter value may be sequential, e.g. the user selects a value for A, then B, then C. Alternatively, the system may display all three parameters in a single display.

Figure 4A:
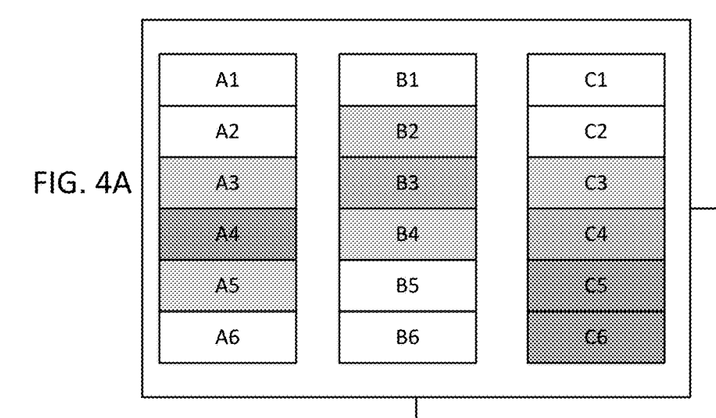
FIGS. 4A-4D illustrate example displays for providing guidance and selecting scan parameters.

FIGS. 4A-D depict three parameters and three sequences of selections. FIG. 4A depicts an initial display of ranges of three parameters highlighted. In FIG. 4A, the recommended ranges may be independent of one another. For example, the ranges of A are not related to the ranges of B or C that are displayed. Each range of values may be separately determined from prior scans or recommendations. Once, however, a value is selected for one of the parameters, the resulting ranges of the other parameters that are provided are related to the first selection.

Figure 4B:
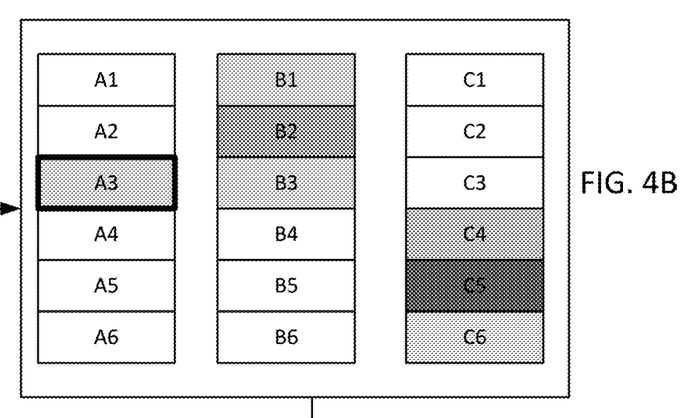
Figure 4C:
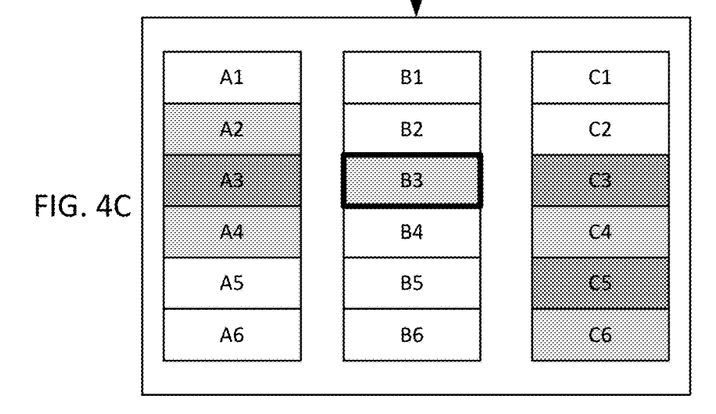
Figure 4D:
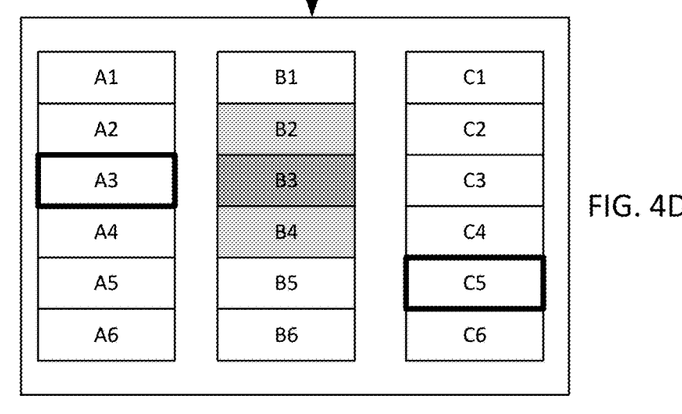

For example, in FIG. 4A and FIG. 4B, once A3 has been selected as a value, the recommended ranges of B and C are updated to B1-B3 and C4-C6. If, as depicted in FIG. 4C, a user selects B3, the values for A and C are updated to reflect the selection. In FIG. 4D, a user has selected both A3 and C5 resulting in a new range of values of B that are recommended. Different values may have different relationships with one another. In one example, the relationship between tube current and patient dose may be linear, with increases in mAs resulting in a comparable percentage increase in patient dose. As a result, after selecting one parameter such as tube current, the other recommendations may change in order to comply with safety or to provide an optimal image. In another example, a smaller pitch, with increased overlap of anatomy and increased sampling at each location, results in an increased radiation dose. Alternatively, a larger pitch implies gaps in the anatomy and hence lower radiation dose. As a result, if all other parameters are unchanged, increasing pitch reduces radiation dose in a linear fashion. If a goal of a user is to decrease radiation dose, the user may select an increased pitch and leave other parameters unchanged.

The selections of values of parameters may be recorded. The result of each scan may be rated by a user to determine a quality score or attributes of an image that result from one or more values for the parameters. The range of selection may be based directly on the recommendations. The most recommended value may be indicated using a visual indication that is distinct from other values. The level or intensity may be based on the level of recommendation. The second most recommended value may be indicated differently than the most recommended and so on. Alternatively, the range of presented selections may be adjusted to, for example, represent a curve of selections with one choice being the most recommend with lesser recommendations falling off in both descending and increasing values. The type or intensity of the visual indication may be based on a level that the value is recommended.

In an embodiment, incompatible results may be greyed out and/or made unavailable for selection. In the example of FIGS. 4A-4D, a selection of value A6 may result in the selection of C1 resulting in an unsafe dose. C1 may then be displayed such that there is an indication to a user that C1 is unsafe or not selectable.

At act A150, the image data is acquired and/or reconstructed using the value of first selection and/or values from subsequent selections. The image data represents a one, two, or three-dimensional region of an object. For example, the image represents an area or slice of a patient as pixel values. A three-dimensional volume may be represented as pixel values by rendering to a two-dimensional format. As another example, the image represents a volume or three-dimensional distribution of voxels. Values are provided for each of multiple locations distributed in two or three dimensions. The image is acquired as a frame of data. The frame of data represents the scan region at a given time or period. The dataset may represent the area or volume over time, such as providing a 4D representation of the patient. Selected values for the acquisition parameters and/or reconstruction parameters are used to acquire the image data and filter the result to provide an image for display to the user of the scan data.

The image may be rated or scored by a user for quality or usefulness. The parameter selections may be recorded by the system. The recorded selections and rated or scored images may provide feedback and training data for analysis and the machine learning model. A threshold for quality may be used for the training images, such as only a score of 5 in a score range of 1-5 where 5 is the best quality. In alternative embodiments, a broader range is used. In yet other embodiments, images of any quality level are used for training the system. A model used to determine values for act A220 may be updated with data from each performed scan as soon as the scans are completed. Alternatively, the model may be static until updated with new data after a specified amount of time.

The ability to provide a choice in multiple parameters allows for flexibility in generating quality scans while still providing recommended guidance. For a new machine, the recommendations and feedback mechanisms may provide different recommendations due to minor differences or different uses of the new machine. The recommendations for different scanners are learnt independently, but based on user feedback for image quality for the respective scanner. By not just running preset protocols, the image quality may be improved over time through experimentation or use.

Figure 5:
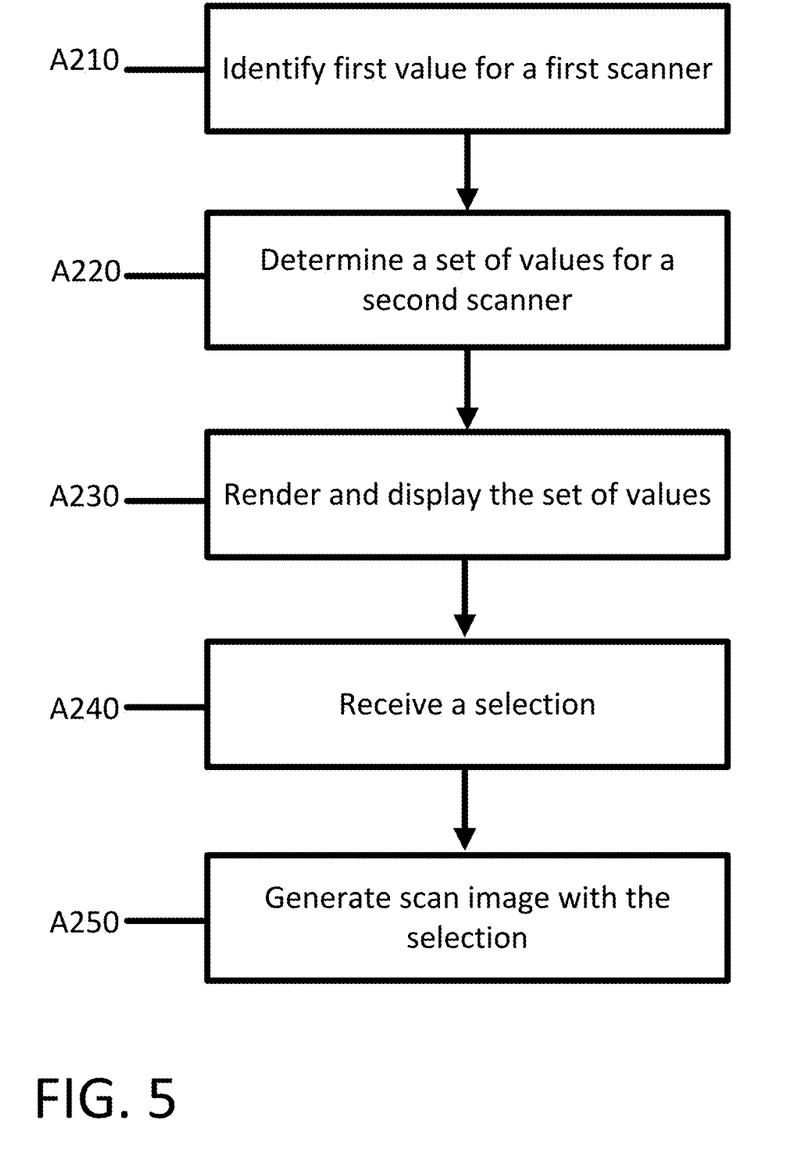
FIG. 5 illustrates one embodiment of a method for providing guidance for converting scan parameters from one scanner to a second scanner.

FIG. 5 illustrates one embodiment of a method for providing guidance for imaging scans. The process includes identifying equivalent parameters between two distinct medical scanners. Analysis of stored data sets for a first and second medical scanners is used to identify relationships between parameters. The relationships between the parameters are provided to a user in a visually distinctive manner.

The acts are performed by the system of FIG. 7, other systems, a medical scanner, a workstation, a computer, and/or a server. For example, acts A210 and A220 are performed by a processing component, such as the medical scanner, a workstation, or a computer. The acts are performed in the order shown (e.g., top to bottom) or other orders.

At act A210, a first value of a scan parameter for a first medical scanner is identified. Different medical scanners (e.g. different manufacturers, models, software) may use different parameters or different terminology or ranges of values for parameters. For example, for scan acquisition parameters in a CT scanner, some models use Tube current time product as a parameter, while other do not. Some models may use automatic exposure control (AEC), a scanner feature that automatically adapts the x-ray tube current to the overall patient size to achieve a specified level of image quality. Some models use Angular and longitudinal tube current modulation, while others may use just Angular or longitudinal. For reconstruction parameters, each model or set of software may include different proprietary or specialized kernels, filters, or algorithms.

At act A220, a set of second values for a scan parameter for a second medical scanner is determined based on the first value. While different scanners may use different parameters, relationships may exist. In a basic conversion, options for one parameter may be scaled differently on one scanner than another. For example, values may be listed in increments of 0.1 on one scanner, while listed on a second scanner in increments of 0.2. While every selection on the second scanner is possible on the first, every selection on the first is not possible on the second scanner (e.g. 0.1, 0.3, 0.5). The set of second values may be the closest approximation for the conversion. For example, if the value for the first scanner is 0.5, the set of second values may be 0.4 and 0.6.

For more complex conversions, machine learning may be used. In certain scenarios, there is not a direct conversion available for parameters. For reconstruction filters, for example, there may be many parameters preset for each filter. A one to one relationship between a first filter on a first scanner and a second kernel on a second scanner may not exist. A statistical or machine learning model may use the results of previous scans on both scanners to determine the set of second values for the scan parameter. To train the model, the model is fed with a set of images that exhibit one or more attributes. Attributes may include but are not limited to quality, sharpness, contrast, blur, resolution, and noise among others.

The machine learning model is any type of machine-learnt classifier that receives input parameters and outputs a classification (e.g., attributes of the image). Support vector machine, Bayesian network, a probabilistic boosting tree, neural network, sparse auto-encoding classifier, or other now known or later developed machine learning may be used. Any semi-supervised, supervised, or unsupervised learning may be used. Hierarchal, cascade, or other approaches may be used.

In one embodiment, a neural network (e.g., deep neural network) is used. Samples of input data with user classified attribute are used to learn to classify the images. For deep learning, the classifier learns the features of the input data to extract from the training data. Alternatively, the features, at least for the input, are manually programmed, such as filtering the scan data and inputting the results of the filtering. The training relates the input data to the classification through one or more layers. One layer may relate feature values to the class. For deep-learnt networks, there may be further layers creating further abstract features from outputs of pervious layers. The resulting machine-trained classifier is a matrix for inputs, weighting, and combination to output a classification and/or probability of class membership. The deep machine-trained classifier includes two or more layers relating the input to the class.

The classifier is trained to output an attribute or score of the image. Any scoring may be used. For example, a numerical range representing sharpness is provided, such as 1-5 or 1-10, where the larger or smaller number represents a sharper image. As another example, alphanumeric classes are used, such as poor quality or good or such as poor, below average, average, good, or excellent quality.

Figure 6A:
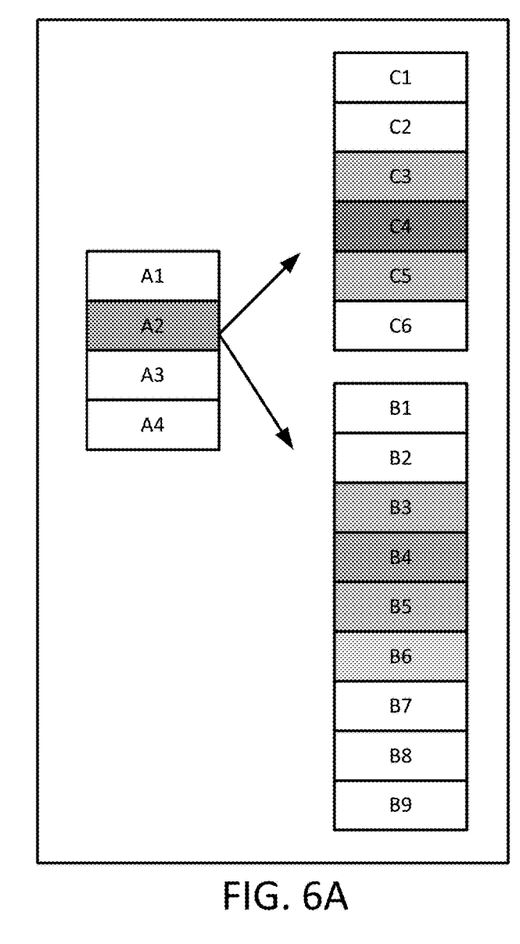
FIGS. 6A and 6B illustrate an example of matching parameters from one scanner to a second scanner.
Figure 6B:
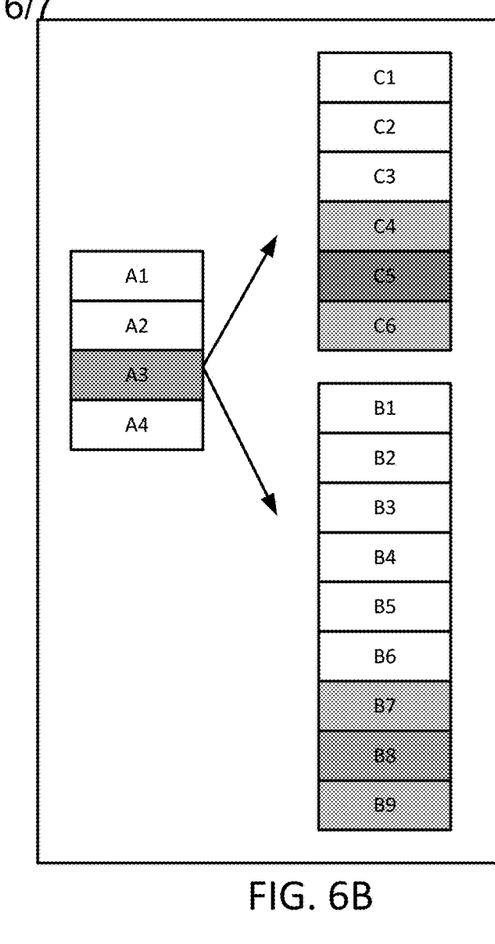

FIGS. 6A and 6B depict examples of a transfer of a parameter from a first scanner to a second scanner. In FIG. 6A, a first scanner uses parameter A to generate a scan image. A second scanner uses parameters B and C to generate a scan image. In the example of FIGS. 6A and 6B, there is not a one to one or direct conversion from the first scanner to the second scanner. In FIG. 6A, the value A2 is selected from the first scanner. A model may determine that when using A2, the resulting image has certain attributes (other parameters may also affect the outcome). The model identifies B and C as affecting a resulting image from the second scanner in a similar way. In FIG. 6A, values of C3-C5 and B3-B6 for the second scanner may produce the same type of image as the selection of A2 for the first scanner. In FIG. 6B, values of C4-C6 and B7-B9 may produce similar images as A3 does when selected for the first scanner.

At act A230, the set of second values is displayed as a highlighted range. Different visual indicators may be used to indicate different advantages or information relating to the different values. Highlighting or shading may be used to provide a visual indication of a level of quality or reasonableness. Different visual techniques may be used to indicate the type of outcome that results from a selection. For example, expected levels of quality or size of the image may be displayed or indicated with the different selections of values.

At act A240, a selection of a second value from the set of second values is received. A user may select the value using an input device such as a touchscreen, keyboard, or microphone. When selected, the value may be displayed with an additional visual indicator such as a different highlight or border.

At act A250, a scan image is generated using the selection. The image data represents a one, two, or three-dimensional region of an object. In an example of the embodiment of FIG. 5, a patient may be scanned with a first scanner at a first time. At a subsequent visit, an operator may wish to perform a second scan. During the interval of time, a new scanner may be used or the software may be updated. In order to compare the first scan and the second scan, it may be beneficial for the two scans to appear similar (e.g. the sharpness of both images should be similar). However, due to the change in machines or software, a user may have difficulty producing the same result due to changes in settings or parameters. In order to produce a similar result, the second scanning system may provide guidance to the user for which values to select to produce a similar image. The generated image at act A250 may be compared to the previous scan image to make a diagnosis.

FIG. 7 shows one embodiment of a system for providing guidance for selecting parameters in a medical image scanner. The system includes an imaging system 540, a server 550, and a database 570. The imaging system includes a processor 530, a memory 520, a display 510, and a scanner 560. Additional, different, or fewer components may be provided. For example, network connections or interfaces may be provided, such as for networking with a medical imaging network or data archival system. In another example, a user interface 580 is provided as part of the display 510 or imaging system 540.

The processor 530, memory 510, display 510, user interface 580, and scanner 560 are part of the imaging system 540. Alternatively, the processor 530 and memory 520 are part of an archival and/or image processing system, such as associated with a medical records database workstation or server, separate from the imaging system 540. In other embodiments, the processor 530 and memory 520, are a personal computer, such as desktop or laptop, a workstation, a server, a network, or combinations thereof. The processor 530, display 510, and memory 520 may be provided without other components for acquiring data by scanning a patient.

The imaging system 540, processor 530, memory 520, display 510, user interface 580, and scanner 560 are provided at a same location. The location may be a same room, same building, or same facility. These devices are local relative to each other and are remote to the server 550. The server 550 is spaced apart by a network by being in a different facility or by being in a different city, county, state, or country. The server 550 and database 570 may be remote from the location of the imaging system 540.

The imaging system 540 is a medical diagnostic imaging system. Ultrasound, computed tomography (CT), x-ray, fluoroscopy, positron emission tomography (PET), single photon emission computed tomography (SPECT), and/or magnetic resonance (MR) systems may be used. The scanner 560 may include a transmitter and includes a detector for scanning or receiving data representative of the interior of the patient.

In one embodiment, the imaging system 540 is a CT system. An x-ray source is connected with a gantry. A detector is also connected with a gantry opposite the x-ray source. The patient is positioned between the source and detector. The source and detector are on opposite sides of the patient and rotate and/or translate about the patient. The detected x-ray energy passing through the patient is converted, reconstructed, or transformed into data representing different spatial locations within the patient.

In another embodiment, the imaging system 540 is a MR system. The MR system includes a main field magnet, such as a cryomagnet, and gradient coils. A whole-body coil is provided for transmitting and/or receiving. Local coils may be used, such as for receiving electromagnetic energy emitted by atoms in response to pulses. Other processing components may be provided, such as for planning and generating transmit pulses for the coils based on the sequence and for receiving and processing the received k-space data. The received k-space data is converted into object or image space data with Fourier processing.

The memory 520 may be a graphics processing memory, a video random access memory, a random-access memory, system memory, cache memory, hard drive, optical media, magnetic media, flash drive, buffer, database, combinations thereof, or other now known or later developed memory device for storing data or video information. The memory 520 is part of the imaging system 540, part of a computer associated with the processor 530, part of a database, part of another system, a picture archival memory, or a standalone device.

The memory 520 stores medical imaging data representing the patient, values of parameters, relationships of parameters, machine-learnt classifiers (e.g., one or more matrices), graphical or display setting, and/or images. The memory 520 may store data during processing for application and/or may store training data (e.g., images and attributes).

The memory 84 or other memory is alternatively or additionally a non-transitory computer readable storage medium storing data representing instructions executable by the programmed processor 530 for analysis of prior scan data. The instructions for implementing the processes, methods and/or techniques discussed herein are provided on non-transitory computer-readable storage media or memories, such as a cache, buffer, RAM, removable media, hard drive, or other computer readable storage media. Non-transitory computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code, and the like, operating alone, or in combination. Likewise, processing strategies may include multiprocessing, multitasking, parallel processing, and the like.

In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

The processor 530 is a general processor, central processing unit, control processor, graphics processor, digital signal processor, three-dimensional rendering processor, image processor, application specific integrated circuit, field programmable gate array, digital circuit, analog circuit, combinations thereof, or other now known or later developed device for analysis of prior scan data. The processor 530 is a single device or multiple devices operating in serial, parallel, or separately. The processor 530 may be a main processor of a computer, such as a laptop or desktop computer, or may be a processor for handling some tasks in a larger system, such as in the imaging system 530. The processor 530 is configured by instructions, design, hardware, and/or software to perform the acts discussed herein.

The processor 530 and/or server 550 are configured to perform the acts discussed above for analysis of the prior scan data. The processor 530 and/or server 550 are configured to provide guidance for selecting scan acquisition and reconstruction parameters. The processor 530 and/or server 550 are configured to identify recommended parameters with a machine-trained model using statistical or machine learning processes. The model may be trained based on prior scan and parameters stored in the database 570 or memory 520. The processor 530 and memory 520 may store images, attributes of the images, and associated parameters for the scans for the imaging system 540. The server 550 and/or database 570 may store images, attributes of the images, and associated parameters for scan from one or more imaging systems 540. The model may be used to generate recommended scan parameters on the display 510 of the image scanner 560. In an embodiment, the matching model may use scan parameters from previous scans on a first machine to provide a range of recommended scan parameters on a second machine.

The processor 530 and/or server 550 is configured to provide recommended parameters to the display 510 or to the memory 520. The processor 530 and/or server 550 may be configured to generate a user interface for selections of scan parameters.

The display 510 is a monitor, LCD, projector, plasma display, CRT, printer, or other now known or later developed devise for outputting visual information. The display 510 receives images, graphics, text, quantities, or other information from the processor 530, memory 520, imaging system 540, and/or server 550. The display 510 is configured to visually distinguish one or more values of one or more parameters for selection by a user.

One or more parameters for scan acquisition or reconstruction are displayed. A range of values for the parameters are highlighted or visually distinguished based on data received from the processor 530 and/or server 550.

The user interface 580 may be configured to receive one or more selections from a user. The user interface 580 may include an input device such as one or more buttons, a keypad, a keyboard, a mouse, a stylus pen, a trackball, a rocker switch, a touch pad, a voice recognition circuit, or other device or component for inputting data. The user interface 580 and the display 510 may be combined as a touch screen that may be capacitive or resistive.

The server 550 connects to the imaging system 540 via a network. The network is a local area, wide area, enterprise, another network, or combinations thereof. In one embodiment, the network is, at least in part, the Internet. Using TCP/IP communications, the network provides for communication between the processor 530 and the server 550. Any format for communications may be used. In other embodiments, dedicated or direct communication is used.

The server 530 is a processor or group of processors. More than one server 530 may be provided. The server 530 is configured by hardware and/or software. In one embodiment, the server 530 performs machine learning with training data in the database 570. The server 530 may acquire and the database 570 may store data from multiple scanning machines.

The database 570 is a memory, such as a bank of memories, for storing training data, such as images and respective parameters. Weights or values of parameters of the model and/or classifier are stored in the database 570 and/or the memory 520.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for indicating recommended settings for data acquisition in a medical scanner, the method comprising:

identifying a scan protocol, the scan protocol including a first parameter including a first plurality of possible values, a second parameter including a second plurality of possible values, and a third parameter including a third plurality of possible values;

rendering and displaying, on a user interface the first plurality of possible values for the first parameter, the second plurality of possible values for the second parameter, and the third plurality of possible values for the third parameter;

identifying one or more prior scans performed with the first parameter;

determining values of the first parameter for the prior scans based on an indication of quality for the one or more prior scans;

generating a first subset of recommended values based on the determination;

rendering and displaying, on the user interface, the first plurality of possible values for the first parameter with the first subset of recommended values rendered visually distinctive from other values of the first plurality of possible values, wherein a higher rendered intensity of shading or color of a recommended value of the first subset of recommended values indicates a higher level of recommendation;

receiving, from the user interface, a first user input that corresponds to a selection of a first selected value for the first parameter;

determining a second subset of recommended values for the second parameter and a third subset of recommended values for the third parameter as a function of the scan protocol and the first selection;

rendering and displaying, on the user interface, the second plurality of possible values for the second parameter with the second subset of recommended values rendered visually distinctive from other values of the second plurality of possible values and the third plurality of possible values for the third parameter with the third subset of recommended values rendered visually distinctive from other values of the third plurality of possible values, wherein a higher rendered intensity of shading or color of a recommended value indicates a higher level of recommendation;

receiving, from the user interface, a second user input that corresponds to a selection of a second selected value for the second parameter;

determining a fourth subset of recommended values for the first parameter and a fifth subset of recommended values for the third parameter as a function of the scan protocol, the first selection, and the second selection;

rendering and displaying, on the user interface, the first plurality of possible values for the first parameter with the fourth subset of recommended values rendered visually distinctive from other values of the first plurality of possible values and the third plurality of possible values for the third parameter with the fifth subset of recommended values rendered visually distinctive from other values of the third plurality of possible values, wherein a higher rendered intensity of shading or color of a recommended indicates a higher level of recommendation;

receiving, from the user interface, a third user input that corresponds to a selection of a third selected value for the second parameter; and generating, using the medical scanner, image data using the first selection, the second selection, and the third selection.

2. The method of claim 1, wherein the first parameter and second parameter are acquisition parameters.

3. The method of claim 1, wherein the first parameter is an acquisition parameter and the second parameter is an image reconstruction parameter.

4. The method of claim 1, wherein the first subset of values comprises at least a range of three recommended values of the first parameter.

5. The method of claim 1, wherein determining comprises:
training a machine-learnt model using the first parameter for the prior scans and the indication of quality for the prior scans.

6. The method of claim 1, wherein the indication of quality is a scoring system comprising user ratings of the prior scans.

7. The method of claim 1, wherein generating comprises generating computed tomography, magnetic resonance, ultrasound, positron emission tomography, or single photon emission computed tomography image.

8. A method for providing guidance for generating a scan image, the method comprising:
identifying a first value of a first scan parameter for a first medical scanner;
determining, using machine learning of similar previous scan data generated by the first medical scanner and a second medical scanner, a set of second values for a second scan parameter for the second medical scanner based on the first value and user feedback of prior scans, wherein the second medical scanner is a different model than the first medical scanner and where there is not a direct conversion available for the first scan parameter and second scan parameter between the first medical scanner and the second medical scanner;
rendering the set of second values as visually distinctive from other values for the second scan parameter, wherein a higher rendered intensity of shading or color of a value of the set of second values indicates a higher level of recommendation;
displaying, the rendered set of second values on a user interface;
receiving, from the user interface, a selection of a second value from the set of second values; and
generating the scan image with the second medical scanner using the selection.

9. The method of claim 8, wherein the first scan parameter and second scan parameter are scan reconstruction kernels.

10. The method of claim 8, wherein generating comprises generating computed tomography, magnetic resonance, ultrasound, positron emission tomography, or single photon emission computed tomography image.

11. A system for providing guidance for selecting a value for a parameter in a medical scanner, the system comprises:
a memory configured to store a plurality of previous scans, first values for a first parameter for each of the previous scans, second values for a second parameter for each of the previous scans, and third values for a third parameter for each of the previous scans;
a processor configured to identify one or more prior scans of the plurality of previous scans performed with the first parameter, determine values of the first parameter for the prior scans based on an indication of quality for the one or more prior scans, identify one or more first recommended values based on the determined values of the first parameter, identify one or more second recommended values of the second values for the second parameters based on the one or more first recommended values, and identify one or more third recommended values of the third values for the third parameters based on the second and third recommended values;
a display configured to display the first values, second values, and the third values with the respective recommended values displayed differently than other values for selection by a user; and
a touchscreen configured to receive a selection of the value from the first recommended values, wherein after selection of the value, the touchscreen is configured to display different respective recommended values than the previous recommended values.

12. The system of claim 11, further comprising:
an image scanner configured to generate an image scan using the selected value.

13. The system of claim 12, wherein the image scanner is a computed tomography scanner.

* * * * *